(12) United States Patent
Yao et al.

(10) Patent No.: US 6,403,817 B1
(45) Date of Patent: Jun. 11, 2002

(54) METHOD FOR PREPARING PROSTAGLANDIN E-TYPE COMPOUND

(75) Inventors: Chi-Hsiang Yao, Taoyuan Hsien; Rung-Tian Suen, Pingtung Hsien; Yu-Liang Liu, Taipei, all of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/791,711

(22) Filed: Feb. 26, 2001

(51) Int. Cl.$^7$ ................................................ C07C 51/16
(52) U.S. Cl. ...................................... 554/140; 584/117
(58) Field of Search ................................ 554/117, 140

Primary Examiner—Deborah D. Carr
(74) Attorney, Agent, or Firm—Bacon & Thomas, PLLC

(57) ABSTRACT

The present invention discloses a method for preparing a prostaglandin E-type compound, in which prostaglandin F-type compound is used as an initiator to generate novel derivative of prostaglandin F-type compound through a silylation reaction, and eventually a prostaglandin E-type compound is obtained through an oxidation and a desilylation reaction.

13 Claims, No Drawings

METHOD FOR PREPARING PROSTAGLANDIN E-TYPE COMPOUND

BACKGROUND OF THE INVENTION

1. Field of the Invention

The present invention relates to a method for preparing a prostaglandin E-type compound, and a novel intermediate generated during producing the same.

2. Related Prior Art

Prostaglandin is a group of compounds with different pharmaceutical activities, wherein the prostaglandin E-type compounds (PGEs) and cyclopentanone substituted derivatives thereof own multiple curative effects, such as loosing the vascular smooth muscle, curing impotence, being a parturifacient, or an inducing medicine. It can also be used to treat the gastric ulcer caused by non-steroid anti-inflammatory drugs (NSAID). Accordingly, the synthesis of prostaglandin E-type compounds and the derivatives thereof are always one of the most important subjects to chemists and pharmacologists.

In the early days, the prostaglandin E-type compounds were directly extracted from bionts, but only few amounts were obtained. Therefore, varied chemical synthesis methods are developed in order to mass-produce the prostaglandin E-type compounds. Among these methods, the most common one is to couple ethylene compounds to the cycle of cyclopentanone, which is disclosed in U.S. Pat. No. 5,618,959, and WO 9,626,891. Another method disclosed in Japanese patent No. 01,074,995 is to cyclize an arachidonic acid by utilizing a catalyst. In addition to the methods aforementioned, it is pretty common to convert other type prostaglandin into prostaglandin E-type compounds, wherein converting the prostaglandin A-type into E-type is the most often as described in U.S. Pat. No. 3,912,725. Additionally, U.S. Pat. No. 3,892,792 (Yankee E. W. etc.,) and J. Chem. Commun., 1972, 1120 have mentioned that $PGE_2$ can be obtained by using trimethylsilyl group for silylating the 11-,15-hydroxyl group of $PGF_{2\alpha}$ with esterified carboxylic group, and then oxidizing the 9-hydoxyl group thereof, and finally carrying out desilylation and hydrolysis reactions. Czech patent No. 265,733 B1 indicates that $PGE_2$ can be produced by oxidizing and desilylating $PGF_{2\alpha}$, which has a silylated 11,15-tert-butyldimethylsilyl group.

In the methods of U.S. Pat. No. 3,892,792 (Yankee E. W. etc.) and J. Chem. Commun., 1972, 1120, esterification of the carboxylic group of $PGF_{2\alpha}$ is necessary before a silylation reaction of the hydroxyl group, by which the acidity can be reduced and desilylation of the protective trimethylsilyl group on the 11-, 15- position can be prevented. However, this method includes at least five steps to produce $PGE_2$. In the prior arts of Corey E. J. etc. (Tetrahedron Lett., 1986, 2199) and Czech patent No. 265,733B1, tert-butyldimethylsilyl group is selected as a protective group according to its excellent stability and uneasily desilylation, so that the esterification of the carboxylic group can be neglected. On the other hand, the excellent stability may result in a demand for the strong corrosive acid, i.e., hydrofluoric acid, in order to remove the tert-butyldimethylsilyl group, which is just disadvantage of operation and scaling-up.

SUMMARY OF THE INVENTION

The object of the present invention is to provide a method for preparing prostaglandin E-type compounds, in which a more stable intermediate is generated, and the desilylation reaction is easily carried out.

The present invention provides a method of preparing prostaglandin E-type compounds of the formula (I),

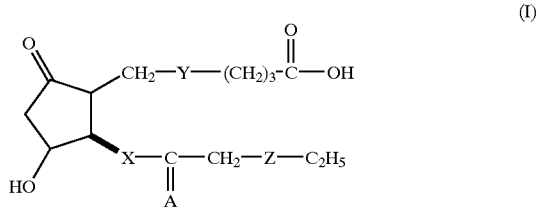

(I)

wherein A is

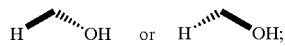

X is trans —CH═CH— or —$CH_2$—$CH_2$—; Y and Z each independently is trans —CH═CH—, cis —CH═CH— or —$CH_2$—$CH_2$—; and pharmaceutically acceptable salts thereof which comprises reacting a compound of the formula (II)

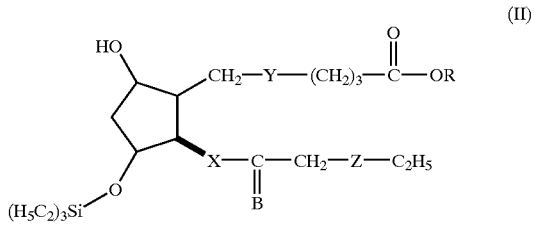

(II)

wherein X, Y and Z are defined as above; R is H or —$Si(C_2H_5)_3$; B is

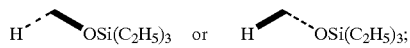

with a Cr(VI)-based reagent or an activated dimethyl sulfoxide reagent in a halogen-containing solvent to proceed an oxidation reaction, and then reacting with an acidic aqueous solution having pH=4~6 in the presence of a water soluble low-boiling-point organic solvent to proceed a desilylation reaction.

The typical compounds of formula (I) are compounds of formula (IV),

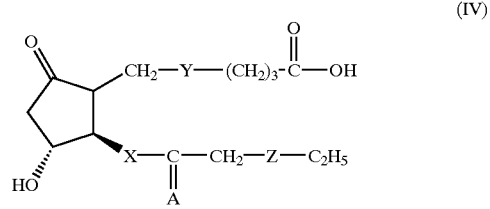

(IV)

wherein A, X, Y and Z is defined as above. The more typical compound of formula (I) is $PGE_2$.

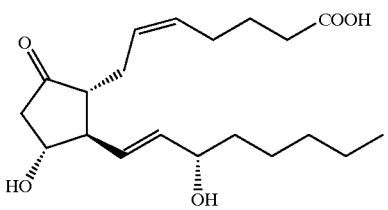

PGE₂

The Cr(VI)-based reagent used in the present invention can be a Collins reagent, pyridinium dichromate (PDC) or pyridinium chlorochromate (PCC). The activated dimethyl sulfoxide reagent can be a Swern reagent or a Corey-Kim reagent. The acidic aqueous solution can be a pyridinium p-toluenesulfonate (PPTS) aqueous solution or an acetic acid aqueous solution. The halogen-containing solvent is selected from the group consisting of dichloromethane, chloroform and dichloroethane. The water-soluble low-boiling-point organic solvent is selected from the group consisting of acetone, acetonitrile, iso-propanol and tetrahydrafuran.

The compound of the formula (II) aforementioned can be obtained by reacting a prostaglandin F-type compound of the formula (III),

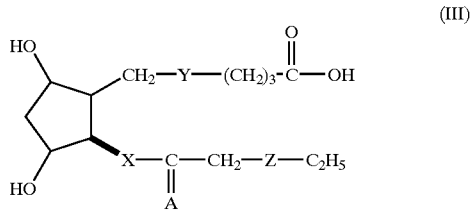

(III)

wherein A, X, Y and Z are defined as above; and a pharmaceutically acceptable salt thereof with N-triethylsilyldiethylamine (TESiD) in a polar organic solvent. The polar organic solvent is selected from the group consisting of acetone, acetonitrile, dichloromethane, dichloroethane, chloroform, tetrahydrafuran, diethyl ether, methyl tert-butyl ether, and methyl ethyl ketone. The compound of the formula (III) can be $PGF_{2\alpha}$.

During the reaction, a novel intermediate of the formula (V) is further generated,

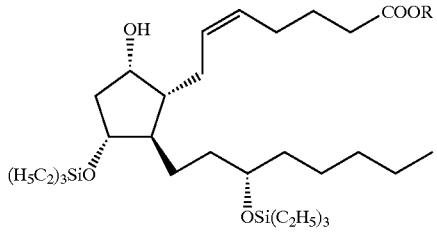

wherein R is H or $-Si(C_2H_5)_3$.

The method of the present invention can be additionally applied to producing correspondent prostaglandin E-type compounds by converting other prostaglandin F-type compounds.

DETAILED DESCRIPTION OF THE PREFERRED EMBODIMENTS

The present invention is related to the method for prostaglandin E-type compounds of formula (I), so that a reaction of $PGE_2$ converting from $PGF_{2\alpha}$ can be used to clearly explain the procedures, and scheme (A) shows such a reaction.

scheme (A)

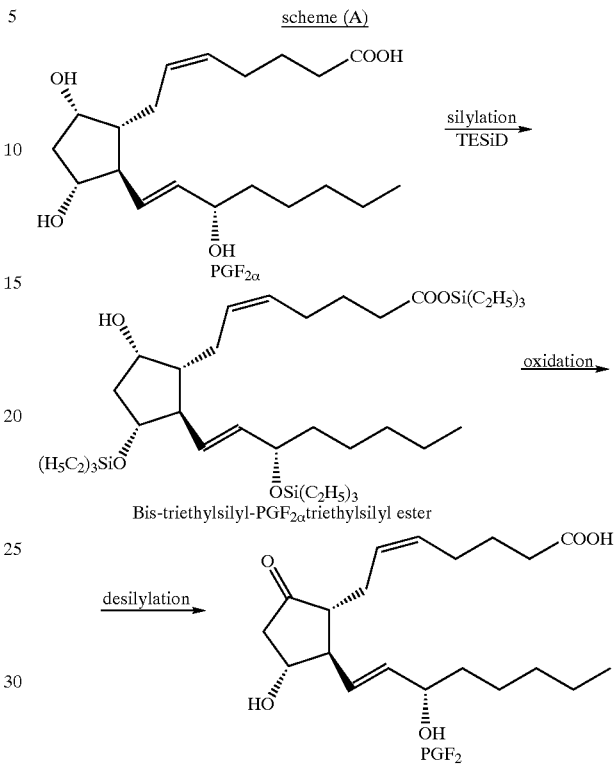

The scheme (A) indicates that a regioselectively silylated compound, i.e., bis-triethylsilyl-$PGF_{2\alpha}$, triethylsilyl ester, can be obtained by reacting $PGF_{2\alpha}$, with TESiD under 15~35° C. for 18~36 hours. Next, the oxidation of the 9-hydroxy group into ketone group is carried out by reacting with a Cr (VI)-based reagent under 15~35° C. for 10~15 minutes or activated dimethyl sulfoxide reagent under −78° C. for 2~3 hours. Last, $PGE_2$ is obtained via a desilylation reaction performed in an acidic aqueous solution reagent having pH=4~6 under 15~35° C. for 12~24 hours.

The examples described below are used for well understanding, but not used to limit the scope of the present invention.

EXAMPLE 1

In the silylation reaction stage, 3.0 g $PGF_{2\alpha}$ and 5.22 g TESiD are dissolved in 30 mL chloroform, and react under 20~30° C. for 24 hours. The solution is then filtered for concentration to obtain 5.9 g bis-triethylsilyl-$PGF_{2\alpha}$, triethylsilyl ester. The analysis result of $^1H$ NMR ($CDCl_3$) is: δ 0.5~0.7 (m, 18H), 0.7~1.1 (m, 30H), 1.1~2.2 (m, 16H), 2.2~2.4 (m, 4H), 3.9~4.1(m, 3H), 5.2~5.5 (m, 4H); and $^{13}C$ NMR ($CDCl_3$): δ4.47, 4.61, 4.94, 6.44, 6.70, 6.86, 13.99, 22.63, 25.03, 25.09, 26.58, 26.71, 31.82, 35.29, 42.95, 38.60, 52.00, 56.44, 73.10, 74.71, 79.72, 129.24, 129.41, 130.88, 134.06, 174.14.

In the oxidation stage, 5.07 g $CrO_3$ and 8.03 g pyridine are added into 60 mL dichloromethane, and stirred under 20~30° C. for 1 hour. 5.90 g bis-triethylsilyl-$PGF_{2\alpha}$, triethylsilyl ester is then added and stirred in the above mixture under 20~30° C. for 10 minutes. Last, 59.0 g silica gel is added into the solution, which is later filtered to obtain 4.1 g intermediate. The analysis result of $^1$H NMR (CDCl$_3$) is: δ 0.4~0.6 (m, 12H), 0.7~1.1 (m, 21H), 1.1~1.8 (m, 10H), 1.9~2.5 (m, 9H), 2.5~2.7 (dd, 1H, J=30, 6Hz), 3.9~4.1 (m, 2H), 5.2~5.4 (m, 2H), 5.4~5.6 (m, 2H); and $^3$C NMR (CDCl$_3$):δ4.66, 4.86, 6.61, 6.74, 13.88, 22.50, 24.39, 24.93, 25.30, 26.44, 31.74, 33.32, 38.39, 47.67, 52.30, 53.65, 72.73, 72.69, 126.69, 128.62, 130.49, 136.12, 178.96, 215.52.

In the desilylation reaction stage, 0.008 g PPTS is first dissolved in 1.6 mL water, which is then added and stirred in a mixture formed by 4.1 g intermediate aforementioned and 20 mL acetone under 20~30° C. until the desilylation reaction is complete. The solvent is then removed, and 82 nL ethyl acetate and 82 mL water are used for extracting the residues. The organic layer is dried by 4.1 g anhydrous sodium sulfate, which is then filtered. The solvent is evaporated, and then 41 mL acetonitrile is added for solving the residues. To purify the product, 82 mL n-hexane is used to extract the product for twice, wherein the desired acetonitrile layer is dried by 4.1 g anhydrous sodium sulfate. After filtration and drying, 2.21 g PGE$_2$ is obtained with a yield of 74%. The m.p. of the product is 68~69° C., and the analysis result of $^1$H NMR (CDCl$_3$) is: δ 0.7~1.1 (t, 3H, J=7Hz), 1.1~1.8 (m, 10H), 1.9~2.5 (m, 9H),2.6~2.8 (dd, 1H, J=30, 6Hz), 3.9~4.1 (m, 2H), 5.2~5.6 (m, 4H); and $^{13}$C NMR (CDCl$_3$): δ14.02, 22.61, 24.39, 25.06, 25.18, 26.30, 31.64, 33.14, 36.82, 46.10, 53.47, 54.46, 72.03, 73.22, 126.64, 130.79, 131.50, 136.53, 177.81, 214.64.

EXAMPLE 2

Repeat the procedure of Example 1, but replace chloroform with acetone, and eventually 2.06 g PGE$_2$ is obtained with a yield of 69%.

EXAMPLE 3

Repeat the procedure of Example 1, but replace CrO$_3$ and pyridine with PDC as an oxidant, and 1.37 g PGE$_2$ is obtained with a yield of 46%.

EXAMPLE 4

Repeat the procedure of Example 1, but replace CrO$_3$ and pyridine with PCC as an oxidant, and 1.22 g PGE$_2$ is obtained with a yield of 41%.

EXAMPLE 5

Repeat the procedure of Example 1, but replace CrO$_3$ and pyridine with Swern reagent as an oxidant to perform an oxidation under −78° C. for 3 hours, and 0.66 g PGE$_2$ is obtained with a yield of 22%.

EXAMPLE 6

Repeat the procedure of Example 1, but replace CrO$_3$ and pyridine with Corey-Kim reagent as an oxidant to perform an oxidation under −78° C. for 3 hours, and 1.73 g PGE$_2$ is obtained with a yield of 58%.

EXAMPLE 7

Repeat the procedure of Example 1, but replace PPTS water solution with acetic acid aqueous solution (pH=4~5), and 2.00 g PGE$_2$ is obtained with a yield of 67%.

According to the Examples of the present invention, varied yields are obtained, and more specially, those of Examples 1, 2 and 7 can even reach above 67%. In the present invention, the prostaglandin F-type compounds are used to react with TESiD under room temperature to obtain regioselectively silylated derivatives of the prostaglandin F-type compounds. Such derivatives are stable enough and easily desilylated, so that the disadvantages of the prior art can be overcome.

Similarly, the method of the present invention can be applied to producing correspondent prostaglandin E-type compounds by converting other prostaglandin F-type compounds.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A method for preparing a prostaglandin E-type compound of the formula (I),

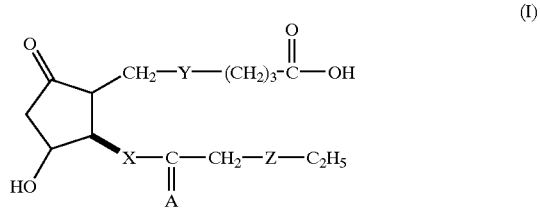

wherein
A is

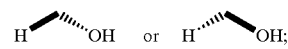

X is trans —CH=CH— or —CH$_2$—CH$_2$—;
Y and Z each independently is trans —CH=CH—, cis—CH=CH— or —CH$_2$—CH$_2$—; and a pharmaceutically acceptable salt thereof, which comprising: reacting a compound of the formula (II)

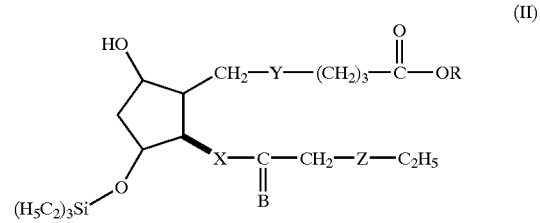

wherein
X, Y and Z are defined as above;
R is H or —Si(C$_2$H$_5$)$_3$;
B is

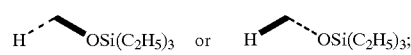

with a Cr(VI)-based reagent or activated dimethyl sulfoxide in a halogen-containing solvent to proceed an oxidation reaction, and then reacting with an acidic aqueous solution having pH=4~6 in the presence of a water-soluble low-boiling-point organic solvent to proceed a desilylation reaction.

2. The method of claim 1, wherein said halogen-containing solvent is selected from the group consisting of dichloromethane, chloroform and dichloroethane.

3. The method of claim 1, wherein said Cr(VI)-based reagent is Collins reagent, pyridinium dichromate or pyridinium chlorochromate.

4. The method of claim 1, wherein said activated dimethyl sulfoxide is Swern reagent or Corey-Kim reagent.

5. The method of claim 1, wherein said water-soluble low-boiling-point organic solvent is selected from the group consisting of acetone, acetonitrile, iso-propanol and tetrahydrafuran.

6. The method of claim 1, wherein said acidic aqueous solution is pyridinium p-toluenesulfonate water solution or acetic acid aqueous solution.

7. The method of claim 1, wherein said compound of the formula (II) is obtained by reacting a prostaglandin F-type compound of the formula (III)

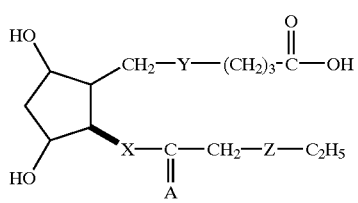

(III)

wherein A, X, Y and Z are defined as above, and a pharmaceutically acceptable salt thereof with N-triethylsilyldiethylamine in a polar organic solvent.

8. The method of claim 7, wherein said polar organic solvent is selected from the group consisting of acetone, acetonitrile, dichloromethane, dichloroethane, chloroform, tetrahydrafuran, diethyl ether, methyl tert-butyl ether, and methyl ethyl ketone.

9. The method of claim 7, wherein said compound of the formula (III) is PGF$_{2\alpha}$.

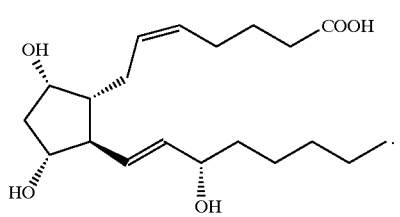

PGF$_{2\alpha}$

10. The method of claim 1, wherein said compound of the formula (I) is a compound of the formula (IV),

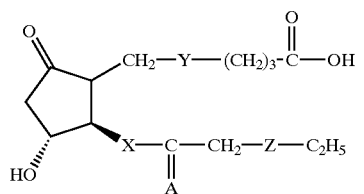

(IV)

wherein A, X, Y and Z are defined as above.

11. The method of claim 1, wherein said compound of the formula (I) is PGE$_2$.

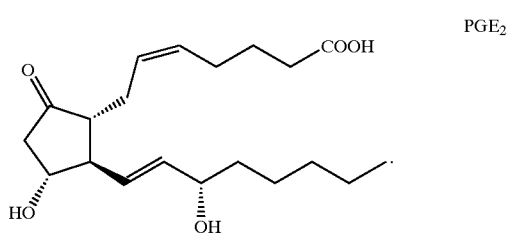

PGE$_2$

12. A compound of the formula (V):

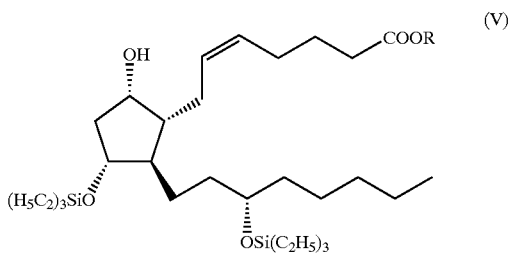

(V)

wherein R is H or —Si(C$_2$H$_5$)$_3$.

13. The compound of claim 12, wherein said R is —Si(C$_2$H$_5$)$_3$.

* * * * *